United States Patent
Reu et al.

(10) Patent No.: US 11,457,970 B2
(45) Date of Patent: *Oct. 4, 2022

(54) INTRAVASCULAR ARTERIAL TO VENOUS ANASTOMOSIS AND TISSUE WELDING CATHETER

(71) Applicant: Avenu Medical, Inc., San Juan Capistrano, CA (US)

(72) Inventors: Gene Reu, San Juan Capistrano, CA (US); Brad M. Kellerman, Escondido, CA (US); David K. Wrolstad, Yucaipa, CA (US)

(73) Assignee: AVENU MEDICAL, INC., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,084

(22) Filed: Jun. 16, 2020

(65) Prior Publication Data

US 2020/0305951 A1 Oct. 1, 2020

Related U.S. Application Data

(60) Continuation of application No. 15/254,754, filed on Sep. 1, 2016, now Pat. No. 10,722,285, which is a (Continued)

(51) Int. Cl.
*A61B 18/08* (2006.01)
*A61B 18/00* (2006.01)

(52) U.S. Cl.
CPC .... *A61B 18/082* (2013.01); *A61B 2018/0013* (2013.01); *A61B 2018/00029* (2013.01); (Continued)

(58) Field of Classification Search
CPC ........ A61B 18/082; A61B 2018/00196; A61B 2018/00404; A61B 2018/0038; (Continued)

(56) References Cited

U.S. PATENT DOCUMENTS

| | | |
|---|---|---|
| 5,290,278 A | 3/1994 | Anderson |
| 5,425,731 A | 6/1995 | Daniel et al. |

(Continued)

FOREIGN PATENT DOCUMENTS

| | | |
|---|---|---|
| WO | 2011159825 A1 | 12/2011 |
| WO | 2012068273 A1 | 5/2012 |
| WO | 2013120021 A1 | 8/2013 |

OTHER PUBLICATIONS

PCT International Search Report and Written Opinion in International Application No. PCT/US2013/070200, dated Mar. 21, 2014, 12 pages.

(Continued)

*Primary Examiner* — Jaymi E Della
(74) *Attorney, Agent, or Firm* — Stinson LLP

(57) ABSTRACT

A device for creating an arteriovenous (AV) fistula includes a proximal base having a distal tapered end surface and a distal tip connected to the proximal base and movable relative to the proximal base. The distal tip has a proximal tapered end surface. A first heating assembly, including an energized heating element, is disposed on at least one of the distal tapered end surface and the proximal tapered end surface. A second heating assembly, comprising a passive non-energized heat spreader, is disposed on the other one of the distal tapered end surface and the proximal tapered end surface. The distal tapered end surface and the proximal tapered end surface are adapted to contact opposing sides of a tissue portion to create the fistula. The taper of the proximal tapered end surface matches the taper of the distal tapered end surface, so that the two surfaces match one another.

22 Claims, 13 Drawing Sheets

Related U.S. Application Data division of application No. 14/080,702, filed on Nov. 14, 2013, now Pat. No. 9,439,710.

(60) Provisional application No. 61/726,544, filed on Nov. 14, 2012.

(52) U.S. Cl.
CPC .............. *A61B 2018/00196* (2013.01); *A61B 2018/00386* (2013.01); *A61B 2018/00404* (2013.01); *A61B 2018/00601* (2013.01); *A61B 2018/00619* (2013.01); *A61B 2018/00642* (2013.01); *A61B 2018/00791* (2013.01)

(58) Field of Classification Search
CPC .. A61B 2018/00386; A61B 2018/0013; A61B 2018/00619; A61B 2018/00791
See application file for complete search history.

(56) References Cited

U.S. PATENT DOCUMENTS

| | | |
|---|---|---|
| 5,553,622 A | 9/1996 | McKown |
| 5,830,222 A | 11/1998 | Makower |
| 5,830,224 A | 11/1998 | Cohn et al. |
| 5,893,369 A | 4/1999 | LeMole |
| 6,024,739 A * | 2/2000 | Ponzi ............... A61B 18/24 |
| | | 600/374 |
| 6,068,637 A | 5/2000 | Popov et al. |
| 6,068,638 A * | 5/2000 | Makower ......... A61B 17/12131 |
| | | 606/159 |
| 6,071,292 A | 6/2000 | Makower et al. |
| 6,083,223 A | 6/2000 | Baker |
| 6,099,542 A | 8/2000 | Cohn et al. |
| 6,190,353 B1 | 2/2001 | Makower et al. |
| 6,235,027 B1 | 5/2001 | Herzon |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,379,319 B1 | 4/2002 | Garibotto et al. |
| 6,398,797 B2 | 6/2002 | Bombard et al. |
| 6,409,721 B1 | 6/2002 | Wheelock et al. |
| 6,464,665 B1 | 10/2002 | Heuser |
| 6,533,778 B2 | 3/2003 | Herzon |
| 6,561,998 B1 | 5/2003 | Roth et al. |
| 6,579,311 B1 | 6/2003 | Makower |
| 6,613,081 B2 | 9/2003 | Kim et al. |
| 6,616,675 B1 | 9/2003 | Evard et al. |
| 6,669,709 B1 | 12/2003 | Cohn et al. |
| 6,699,245 B2 | 3/2004 | Dinger et al. |
| 6,709,444 B1 | 3/2004 | Makower |
| 6,726,677 B1 | 4/2004 | Flaherty et al. |
| 6,863,684 B2 | 3/2005 | Kim et al. |
| 6,908,463 B2 | 6/2005 | Treat et al. |
| 6,929,009 B2 | 8/2005 | Makower et al. |
| 7,056,325 B1 | 6/2006 | Makower et al. |
| 7,074,220 B2 | 7/2006 | Hill et al. |
| 7,159,592 B1 | 1/2007 | Makower et al. |
| 7,191,015 B2 | 3/2007 | Lamson et al. |
| 7,316,655 B2 | 1/2008 | Garibotto et al. |
| 7,351,247 B2 | 4/2008 | Kupiecki et al. |
| 7,387,636 B2 | 6/2008 | Cohn et al. |
| 7,588,566 B2 | 9/2009 | Treat et al. |
| 7,729,738 B2 | 6/2010 | Flaherty et al. |
| 7,846,172 B2 | 12/2010 | Makower |
| 7,988,690 B2 | 8/2011 | Chanduszko et al. |
| 8,236,014 B2 | 8/2012 | Brenneman et al. |
| 8,721,639 B2 | 5/2014 | Mirizzi et al. |
| 8,834,518 B2 | 9/2014 | Faller et al. |
| 2002/0188294 A1 | 12/2002 | Couture et al. |
| 2003/0040764 A1* | 2/2003 | Adams ............... A61B 1/00154 |
| | | 606/170 |
| 2003/0129382 A1 | 7/2003 | Treat |
| 2003/0225426 A1 | 12/2003 | Hill |
| 2003/0229344 A1* | 12/2003 | Dycus ................ A61B 18/1445 |
| | | 606/51 |
| 2004/0073238 A1 | 4/2004 | Makower |
| 2004/0082945 A1 | 4/2004 | Clague |
| 2004/0204725 A1 | 10/2004 | Bayer |
| 2005/0020265 A1 | 1/2005 | Voegele |
| 2005/0033330 A1 | 2/2005 | Vargas et al. |
| 2005/0038457 A1 | 2/2005 | Vargas et al. |
| 2006/0020265 A1 | 1/2006 | Ryan |
| 2006/0111704 A1 | 5/2006 | Brenneman et al. |
| 2006/0142788 A1 | 6/2006 | Wilson et al. |
| 2006/0189979 A1 | 8/2006 | Esch et al. |
| 2006/0217706 A1* | 9/2006 | Lau ..................... A61B 18/1445 |
| | | 606/45 |
| 2007/0112348 A1 | 5/2007 | Eggers et al. |
| 2007/0175963 A1* | 8/2007 | Bilotti .................. A61B 17/115 |
| | | 227/179.1 |
| 2007/0276363 A1 | 11/2007 | Patton |
| 2008/0187989 A1* | 8/2008 | McGreevy ........... A61B 18/085 |
| | | 435/284.1 |
| 2008/0312651 A1 | 12/2008 | Pope et al. |
| 2009/0048589 A1* | 2/2009 | Takashi .............. A61B 18/1445 |
| | | 606/28 |
| 2009/0312783 A1 | 12/2009 | Whayne |
| 2010/0152723 A1 | 6/2010 | Esch et al. |
| 2010/0204698 A1 | 8/2010 | Chapman et al. |
| 2011/0011916 A1 | 1/2011 | Levine |
| 2011/0095067 A1 | 4/2011 | Ohdaira |
| 2011/0251608 A1 | 10/2011 | Timm et al. |
| 2011/0251609 A1 | 10/2011 | Johnson et al. |
| 2011/0288546 A1 | 11/2011 | Abbott et al. |
| 2011/0306959 A1 | 12/2011 | Kellerman et al. |
| 2012/0016413 A1 | 1/2012 | Timm |
| 2012/0078246 A1 | 3/2012 | Mirizzi et al. |
| 2012/0302935 A1 | 11/2012 | Miller et al. |
| 2012/0316550 A1 | 12/2012 | Lau et al. |
| 2013/0281998 A1 | 10/2013 | Kellerman et al. |
| 2014/0142561 A1 | 5/2014 | Reu et al. |

OTHER PUBLICATIONS

PCT International Preliminary Report on Patentability in International Application No. PCT/US2013/070200, dated May 19, 2015, 9 pages.

European Office Action in European Application No. 13855143.7, dated Apr. 22, 2021, 12 pages.

International Search Report and Written Opinion in related PCT Application US2013/070200. International Filing Date Nov. 14, 2013.

Supplementary European Search Report dated Jun. 17, 2016 in connection with corresponding EPO App. No. 13855143.7.

Office Action dated Jan. 31, 2017 in connection with corresponding Japan Pat. App. No. 2015-542793.

Examination Report dated May 23, 2017 in connection with corresponding Australian Pat. App. No. 2013344595.

Office Action dated Apr. 11, 2019 in connection with corresponding Canadian Pat. App. No. 2,891,257.

Examination Report from EP Application No. 13855143.7, dated Sep. 21, 2021, 4 pages.

* cited by examiner

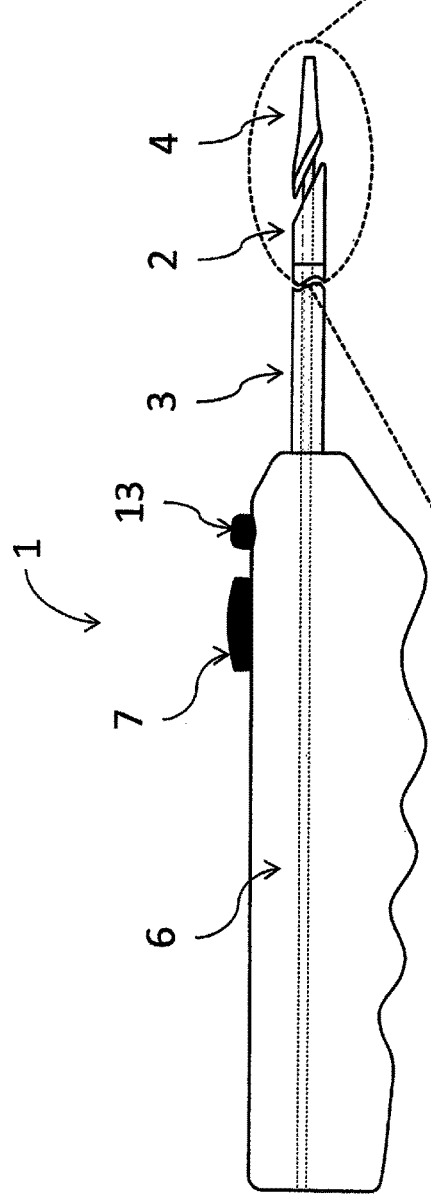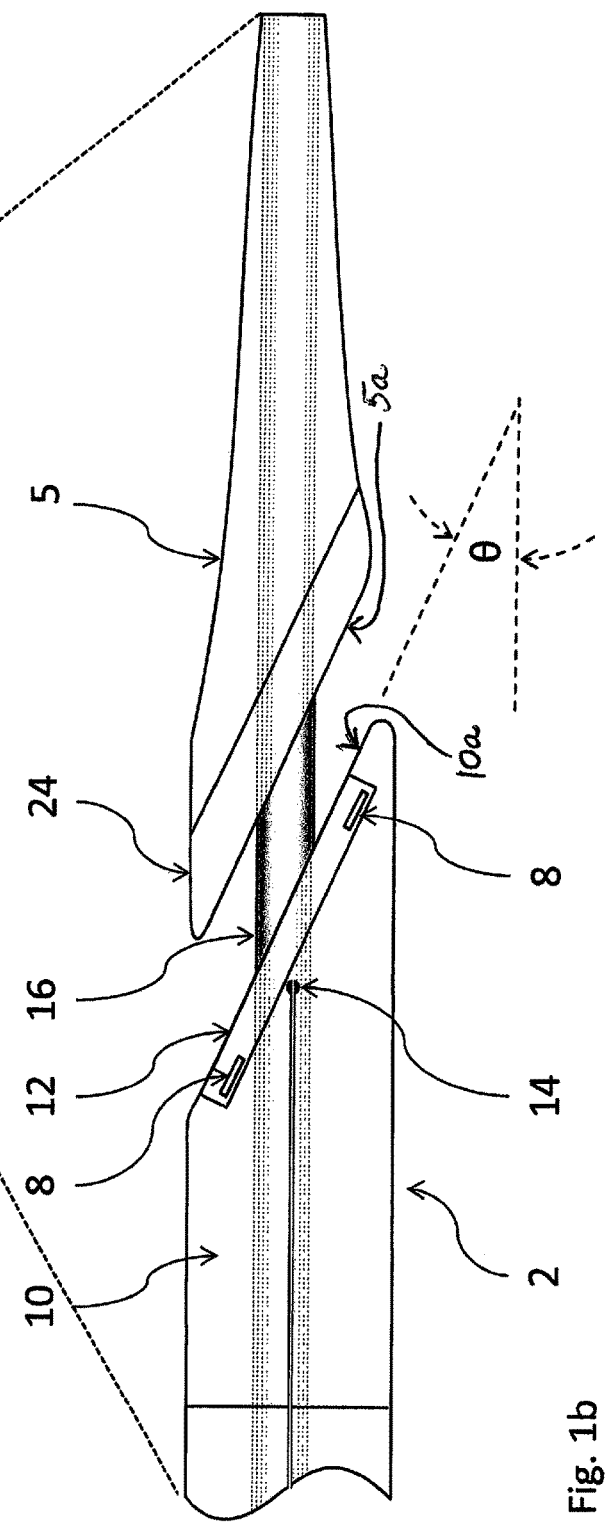
Fig. 1a
Fig. 1b

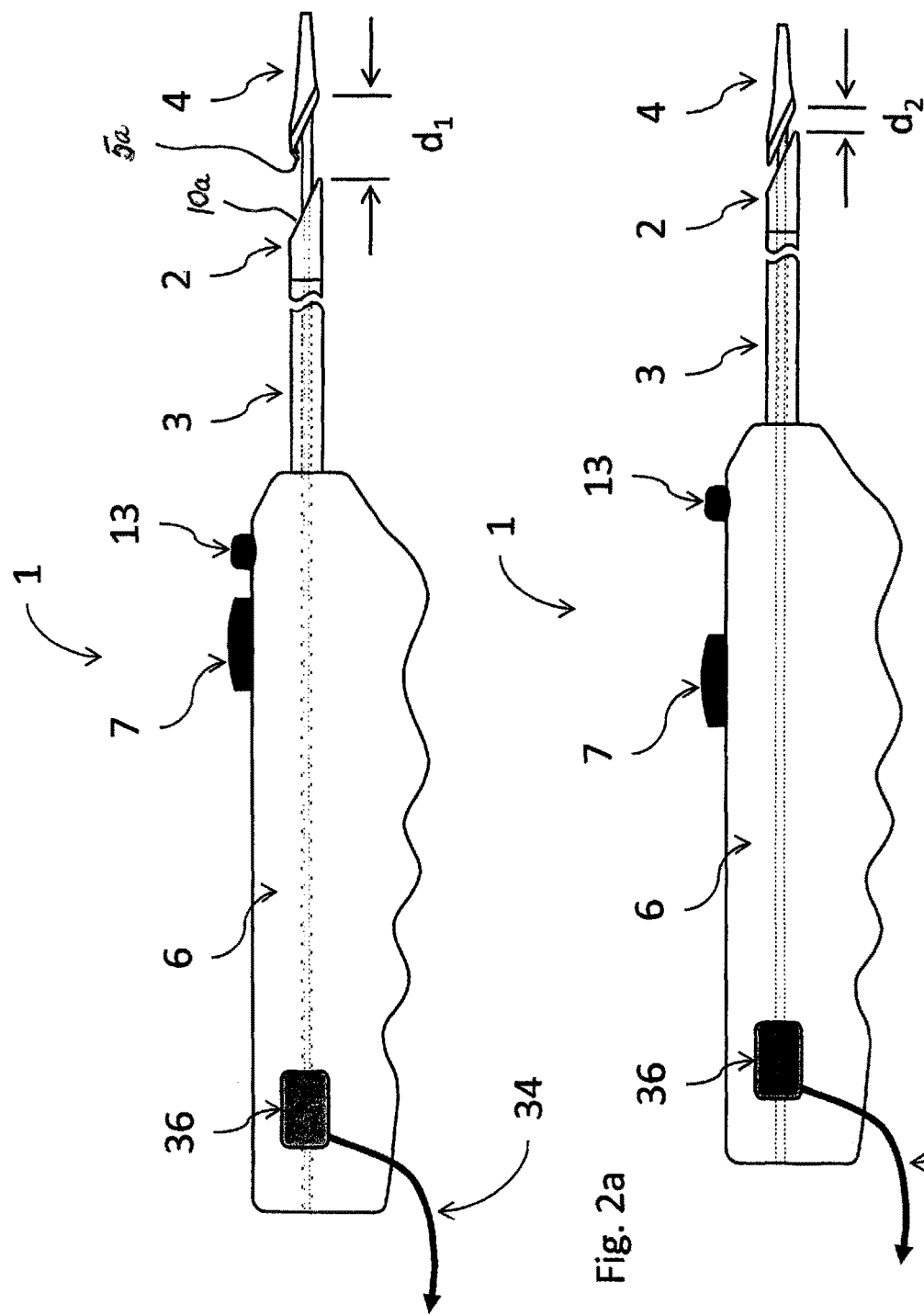

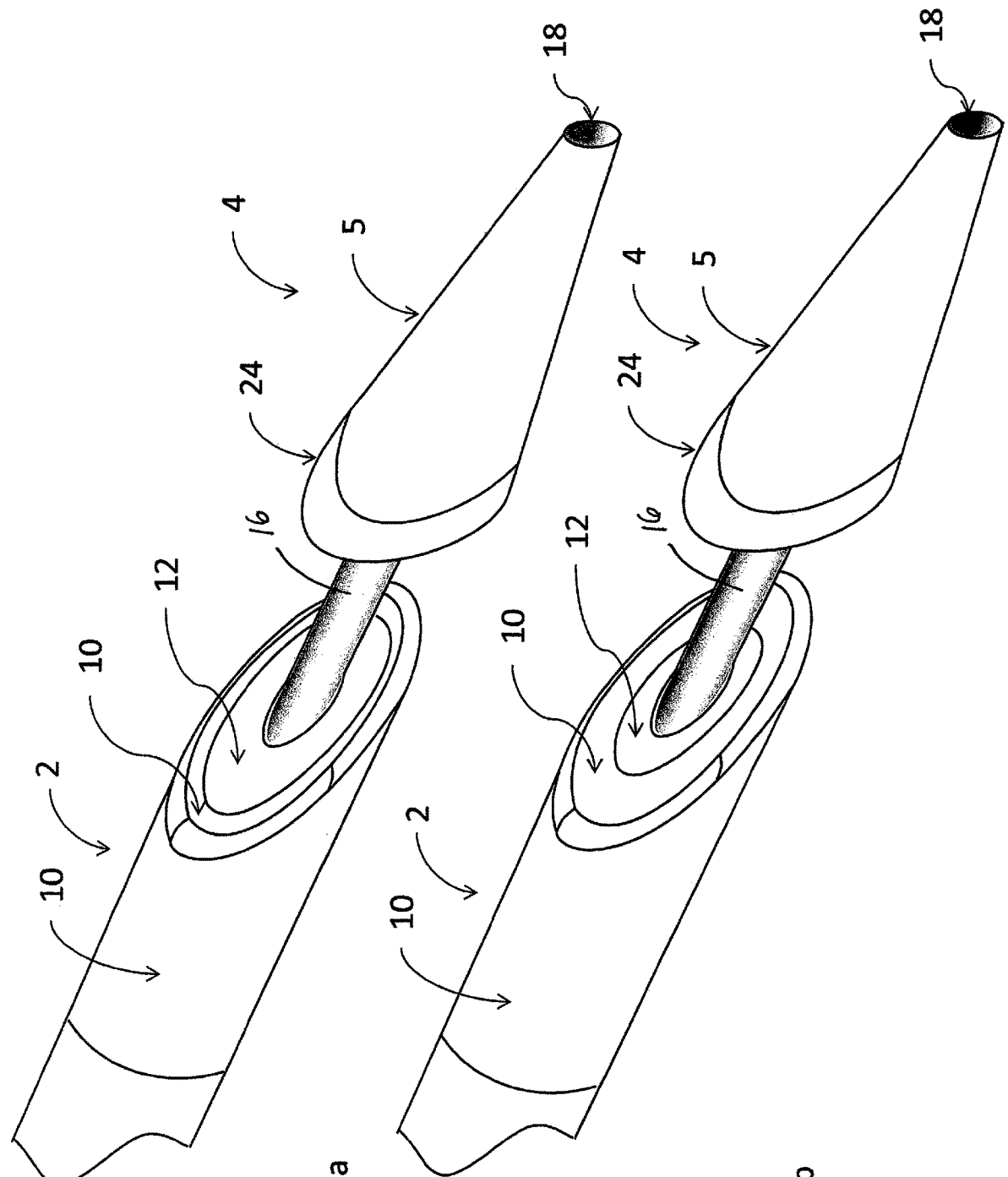

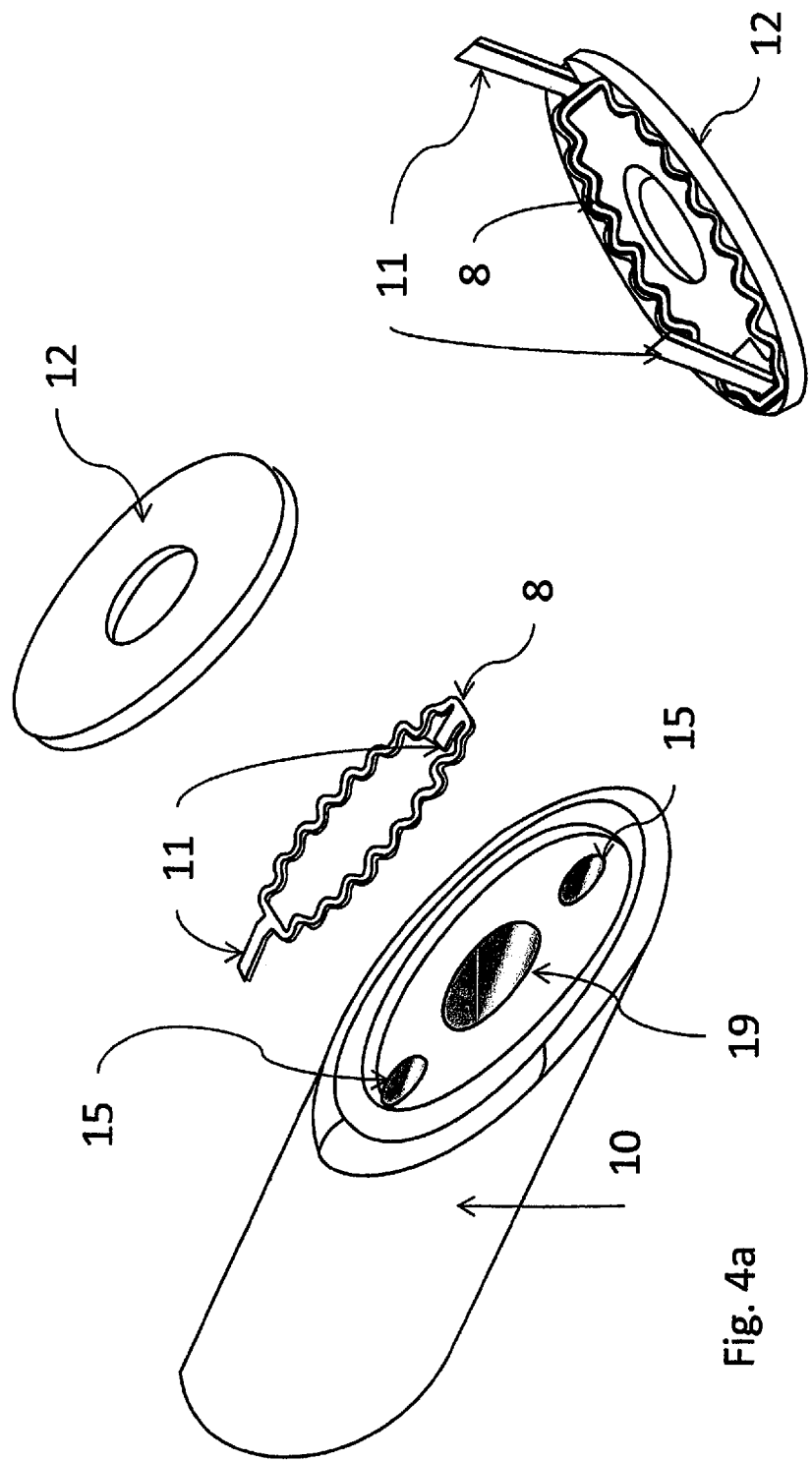

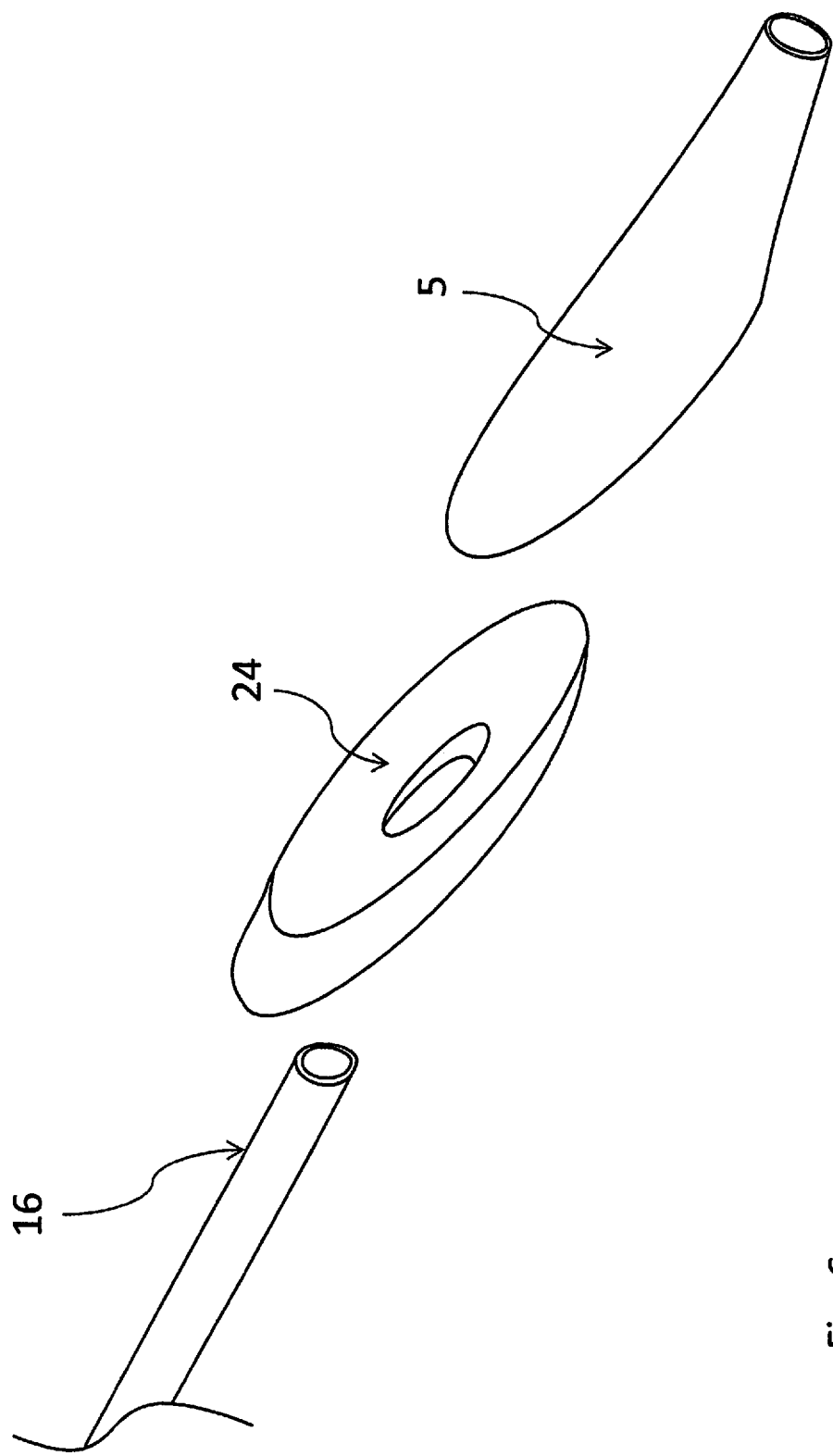

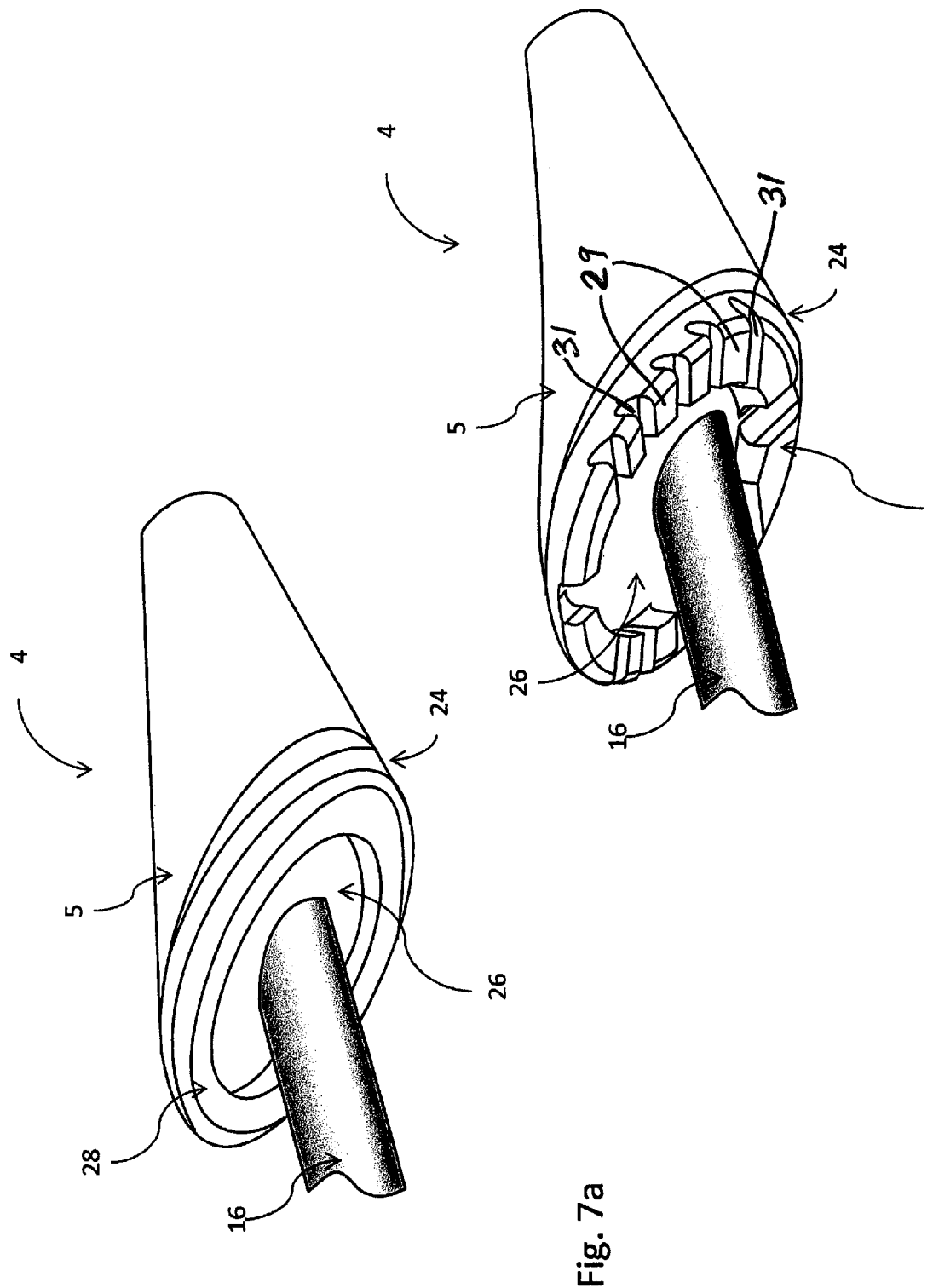

INTRAVASCULAR ARTERIAL TO VENOUS ANASTOMOSIS AND TISSUE WELDING CATHETER

This application is a continuation under 35 U.S.C. 120 of commonly assigned U.S. application Ser. No. 15/254,754, filed on Sep. 1, 2016 and entitled Intravascular Arterial to Venous Anastomosis and Tissue Welding Catheter, now issued as U.S. Pat. No. 10,722,285, which in turn is a divisional under 35 U.S.C. 120 of commonly assigned U.S. application Ser. No. 14/080,702, filed on Nov. 14, 2013 and entitled Intravascular Arterial to Venous Anastomosis and Tissue Welding Catheter, now U.S. Pat. No. 9,439,710, which in turn claims the benefit under 35 U.S.C. 119(e) of the filing date of Provisional U.S. Application Ser. No. 61/726,544, entitled Intravascular Arterial to Venous Anastomosis and Tissue Welding Catheter, filed on Nov. 14, 2012. Each of the foregoing applications are herein expressly incorporated herein by reference, in their entirety.

This application is related to U.S. application Ser. No. 13/161,356, entitled Intravascular Arterial to Venous Anastomosis and Tissue Welding Catheter, filed on Jun. 15, 2011, to U.S. Provisional Application Ser. No. 61/596,670, entitled Intravascular Arterial to Venous Anastomosis and Tissue Welding Catheter, filed on Feb. 8, 2012, and to U.S. application Ser. No. 13/668,190, entitled Systems and Methods for Percutaneous Intravascular Access and Guidewire Placement, filed on Nov. 2, 2012. Each of these applications are also each expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with (1) catheters placed in large veins, (2) prosthetic grafts attached to an artery and a vein, or (3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater, in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialysed and non-dialysed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present invention comprises a device for creating an arteriovenous (AV) fistula, which comprises a proximal base having a distal tapered end surface and a distal tip connected to the proximal base and movable relative to the proximal base. The distal tip has a proximal tapered end surface. A first heating assembly, comprising an energized heating element, is disposed on at least one of the distal tapered end surface and the proximal tapered end surface. A second heating assembly, comprising a passive non-energized heat spreader, is disposed on the other one of the distal tapered end surface and the proximal tapered end surface. The distal tapered end surface and the proximal tapered end surface are adapted to contact opposing sides of a tissue portion to create the fistula. The distal tapered end surface is oriented at an angle of 15-90 degrees relative to a longitudinal axis of the device, and more advantageously at an angle of 15-50 degrees relative to the longitudinal axis. In one particularly optimal configuration, the distal tapered end surface is oriented at an angle of approximately 23 degrees relative to the longitudinal axis. The taper of the proximal tapered end surface matches the taper of the distal tapered end surface, so that the two surfaces match one another and fully engage with one another when engaged.

A shaft is provided for connecting the distal tip to the proximal base, the shaft being extendable and retractable to extend and retract the distal tip relative to the proximal base.

The tapered end surface on which the heating assembly is disposed preferably has a second passive non-energized heat spreader disposed thereon. The energized heating element optimally comprises a serpentine configuration. A temperature sensor is disposed near the energized heating element, for providing closed loop temperature control to the heating assembly.

The second heat spreader comprises a thermally conductive material which extends across a substantial portion of the tapered end surface on which it is disposed, the second heat spreader being in thermal contact with the energized heating element to draw heat from the heating element and spread the heat across the tapered end surface. It is constructed so that it has a thickness approximately equal to a thickness of a vessel in which the device is deployed, this thickness falling within a range of 0.010 inches to 0.060 inches.

In one configuration, the heat spreader comprises a plurality of raised segments forming a segmented rib, for creating a focused heat conduction path through tissue. The segmented rib further comprises gaps between the segments, which gaps provide an insulative barrier that limits tissue dessication to promote adhesion without cutting. In another configuration, the heat spreader comprises a raised outer rib along its circumference, the raised outer rib forming a pocket in a center portion thereof for capturing and removing tissue removed. An outer circumference of the rib comprises a radius for creating a transition between a weld band outside of a cut zone formed during a procedure and native tissue.

In other embodiments, the heat spreader comprises a domed surface, or comprises a raised center surface and a lower profile outer surface.

The distal tip comprises a tapered outer surface, tapering down from the proximal tapered end surface toward a distal end thereof, the distal end of the distal tip comprising an aperture for a through lumen for receiving a guidewire, wherein a width of the distal tip at the lumen aperture is approximately equal to a diameter of a guidewire.

The energized heating element comprises separate elliptical elements that provide independent power delivery for heating and cutting. The separate elliptical elements comprise an outer element and an inner element, the outer element being configured to deliver reduced heat to promote controlled dessication and adhesion in a weld zone without cutting through tissue and the inner element being configured to deliver increased heat to promote rapid cutting through tissue in a cutting zone.

In illustrated embodiments, the first heating assembly is disposed on the distal tapered end surface and the second heating assembly is disposed on the proximal tapered end surface.

A second active energized heating element is provided on the proximal tapered end surface in some embodiments, which is embedded into the heat spreader.

Each of the first and second heating assemblies preferably comprise non-stick surfaces, and the shaft also preferably comprises a non-stick surface. The non-stick surfaces have a surface finish of less than 16 Ra.

A position sensor is provided for monitoring movement of the distal tip.

In another aspect of the invention, there is provided a method for creating an arteriovenous (AV) fistula, which comprises steps of selecting an appropriate procedural site having each of a primary blood vessel and a secondary blood vessel in close proximity to one another, inserting a piercing device into the primary vessel to pierce the vessel walls and creating an opening so that the piercing device extends into the adjacent secondary vessel, and advancing a guidewire until the guidewire is positioned in a blood flow path of the secondary vessel sufficiently to allow the piercing device to be removed. The piercing device is then withdrawn. A proximal end of the guidewire is loaded into a lumen of a distal tip of a device for creating the AV fistula, and the device is advanced over the guidewire until a tapered dilating distal tip of the device comes into contact with the selected anastomosis site. The distal tip of the device is advanced relative to a proximal base of the device to thereby dilate the opening in the second vessel, so that the distal tip is in the second vessel and the proximal base is in the first vessel.

At this juncture, a heat spreader on an angled distal surface of the proximal base is seated against an inner wall of the first vessel surrounding the opening. The distal tip is retracted so that a heat spreader on an angled proximal surface of the distal tip seats against an inner wall of the second vessel surrounding the opening, thereby capturing the walls of the first and second vessel between the facing angled surfaces of each of the distal tip and the proximal base, respectively.

A controlled tension is maintained between the distal tip and the proximal base, and at the same time energy is applied to a heating element on the distal angled surface of the proximal base. The resultant applied heat and pressure forms a fistula with welded edges defining the fistula opening. The device is then withdrawn from the procedural site.

The invention, together with additional features and advantages thereof, may best be understood by reference to the following description taken in conjunction with the accompanying illustrative drawings.

BRIEF DESCRIPTION OF THE DRAWINGS

FIG. 1a is an elevational view of the handle portion of a device constructed in accordance with one embodiment of the present invention;

FIG. 1b is an elevational enlarged view of the circled distal working portion of the device of FIG. 1a;

FIG. 2a is an elevational view of an embodiment like that shown in FIGS. 1a-1b, with the distal end in a first working configuration;

FIG. 2b is an elevational view similar to FIG. 2a, with the distal end in a second working configuration;

FIG. 3a is an isometric view of one embodiment of the device shown in FIGS. 1a-2b;

FIG. 3b is an isometric view similar to FIG. 3a illustrating a modified embodiment of the heating mechanism;

FIG. 4a is an exploded isometric view illustrating an embodiment of the proximal base and particularly showing the assembly of the heating element and proximal heat spreader;

FIG. 4b is an isometric view showing the assembled heating element and proximal heat spreader;

FIG. 6 is an exploded isometric view of an embodiment of the distal tip and distal heat spreader;

FIG. 7a is an isometric view of one embodiment of the distal tip and heating assembly of the present invention;

FIG. 7b is an isometric view similar to FIG. 7a of a modified embodiment of the distal tip and heating assembly of the present invention;

FIG. 11a is an elevational view similar to FIG. 1a illustrating a modified embodiment of the device of FIG. 1a, but having an active distal heater rather than a passive heat spreader; and FIG. 11b is an elevational enlarged view of the circled portion of FIG. 11a.

DESCRIPTION OF THE PREFERRED EMBODIMENT

Figure 4C:
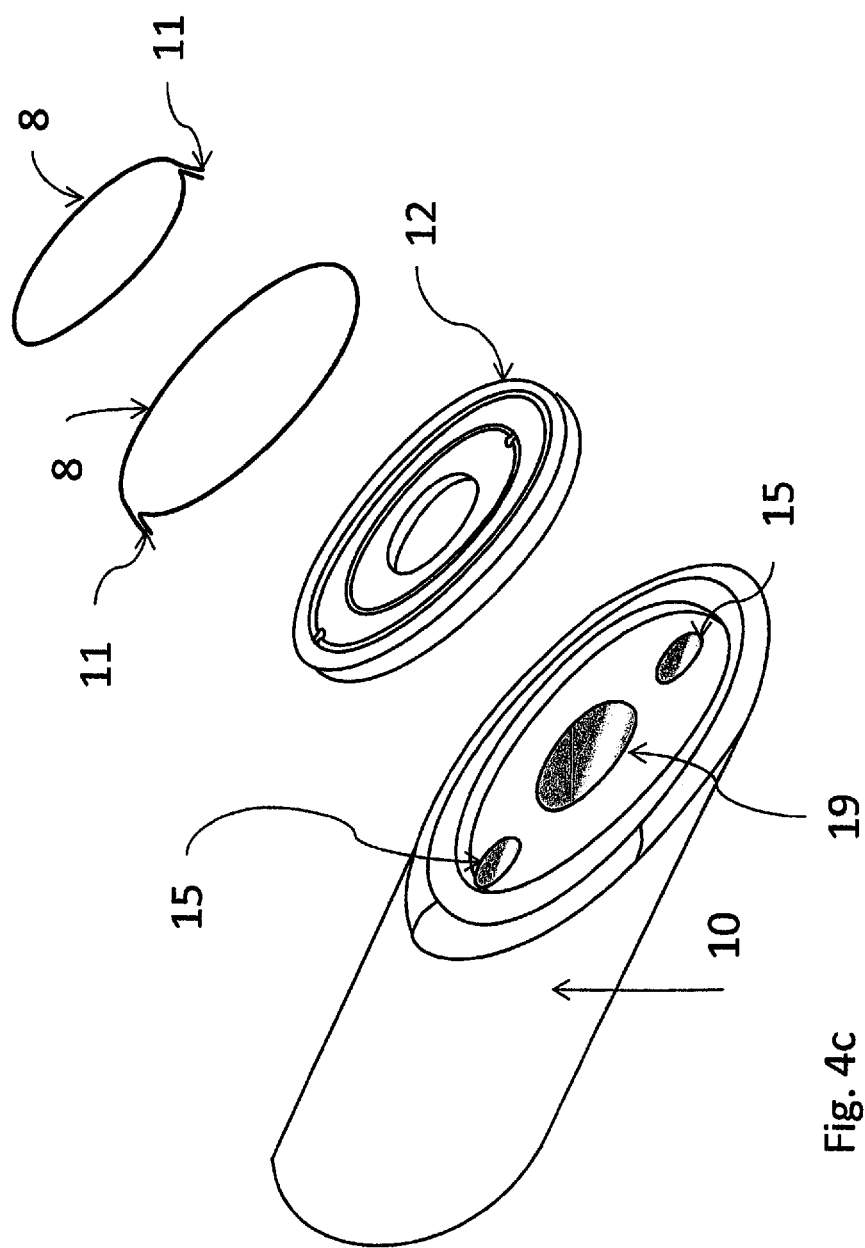
FIG. 4c is an exploded isometric view similar to FIG. 4a showing a modified embodiment of the proximal heating assembly.

Referring now more particularly to the drawings, as illustrated in FIGS. 1a and 1b, one embodiment of the inventive intraluminal anastomotic device 1 comprises four main components, including a proximal heating assembly 2, a proximal shaft 3, a distal heating assembly 4, and a handpiece 6. The distal heating assembly 4 comprises a distal tip 5 and heat spreader 24. The handpiece 6 comprises a tip actuation button 7 and a release button 13. The proximal heating assembly 2 is constructed of a proximal base 10 that is cut at an angle θ at the distal end. In one embodiment, the proximal base 10 is cut at an angle θ of 23 degrees, forming an angled distal tapered end surface 10a. However, the angle θ can be adjusted depending on the particular anatomy of a procedural site and desired anastomosis length. The inventors have found that the angle θ provides advantageous outcomes within a range of about 15-90 degrees, and more particularly within a range of 15-50 degrees, keeping in mind that approximately 23 degrees is presently a particularly preferred angle within that range. These preferred angles/angle ranges result in an optimized oval configuration for the anastomosis which maximizes the cutting surface while also efficiently utilizing available heating energy to create an effective cut and welding zone.

On the angled surface 10a of the proximal base 10, a heating element 8 is embedded. The proximal base 10 is typically constructed of a thermally insulating material that is resistive to high temperatures. Materials known to work well for this application include Vespel, Celazol, Teflon, Polyimide, Ultem, and ceramics. A proximal heat spreader 12 is used to compress and heat the tissue to create coaptation of vessel tissues. This process is known as tissue welding or tissue fusion. In one embodiment, the proximal heat spreader 12 is constructed of a thermally conductive material with the resistive heating element embedded therein. Some examples of thermally conductive material suitable for this purpose include aluminum, stainless steel, aluminum nitride, or other metal or ceramic materials known to those skilled in the art. The position, size, and shape of the proximal heat spreader 12 can be adjusted to control where the heat is applied to tissue (see FIGS. 3a and 3b for exemplary alternative embodiments). For example, it may be beneficial to place the proximal heat spreader 12 toward the center of the long axis of the device body (FIG. 3b), such that a heat gradient is created across the face of the angled surface of the proximal base 10. This provides the tissue near the center of the cutting region with the most heat, which completely denatures the tissue, and less heat radially outwardly of the center, to limit the amount of necrosis, while still providing strong coaptation or welding of the tissues. The proximal base 10 is configured with at least one thermocouple or temperature sensor 14 to monitor the temperature near the active heating element 8, and provides a means for closed loop temperature control to optimize tissue welding and cutting.

As illustrated particularly in FIGS. 6 and 7a-7c, the distal tip 5 comprises a uniform conical tapered outer surface, though it can have a variable tapered, sloped outer surface as illustrated in FIGS. 8a-8f, wherein the outer surface tapers down to the approximate diameter of a guidewire to provide an atraumatic method for passing through the vessel wall. A guidewire lumen 18 extends through the center of the distal tip 5, as shown in FIGS. 3a and 3b. In one particular embodiment, the lumen 18 is sized to receive a 0.014 inch guidewire, but may be sized to receive guidewires of various diameters. The intraluminal anastomotic device 1 is tracked over a guidewire 17 (FIG. 9) and the tapered outer surface of the distal tip 5 dilates through the tissue into the adjacent vessel. Once the distal heating assembly 4 is completely disposed within the adjacent vessel, the distal tip 5 is retracted to bring the tip toward the proximal heating assembly 2, thereby capturing vessel wall tissue between the two components 5 and 10, and bringing the adjacent walls of a first vessel 20 and a second vessel 22 together. A proximal end surface 5a of the distal heating assembly 4 is angled to precisely match the angle θ of the proximal heating assembly 2.

Figure 9:
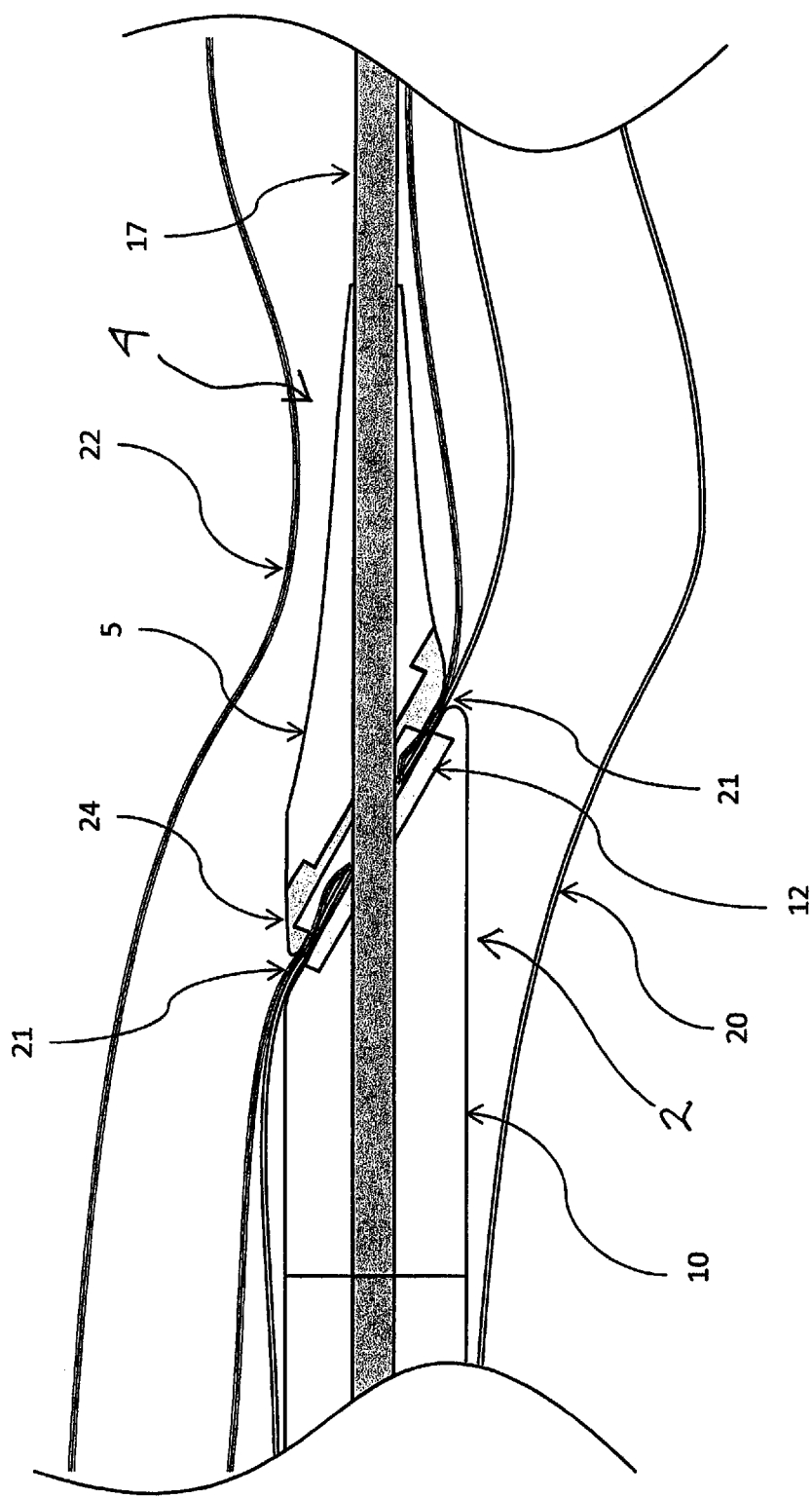
FIG. 9 is a cross-sectional view showing an application and method of using the device and system of the present invention.
Figure 10:
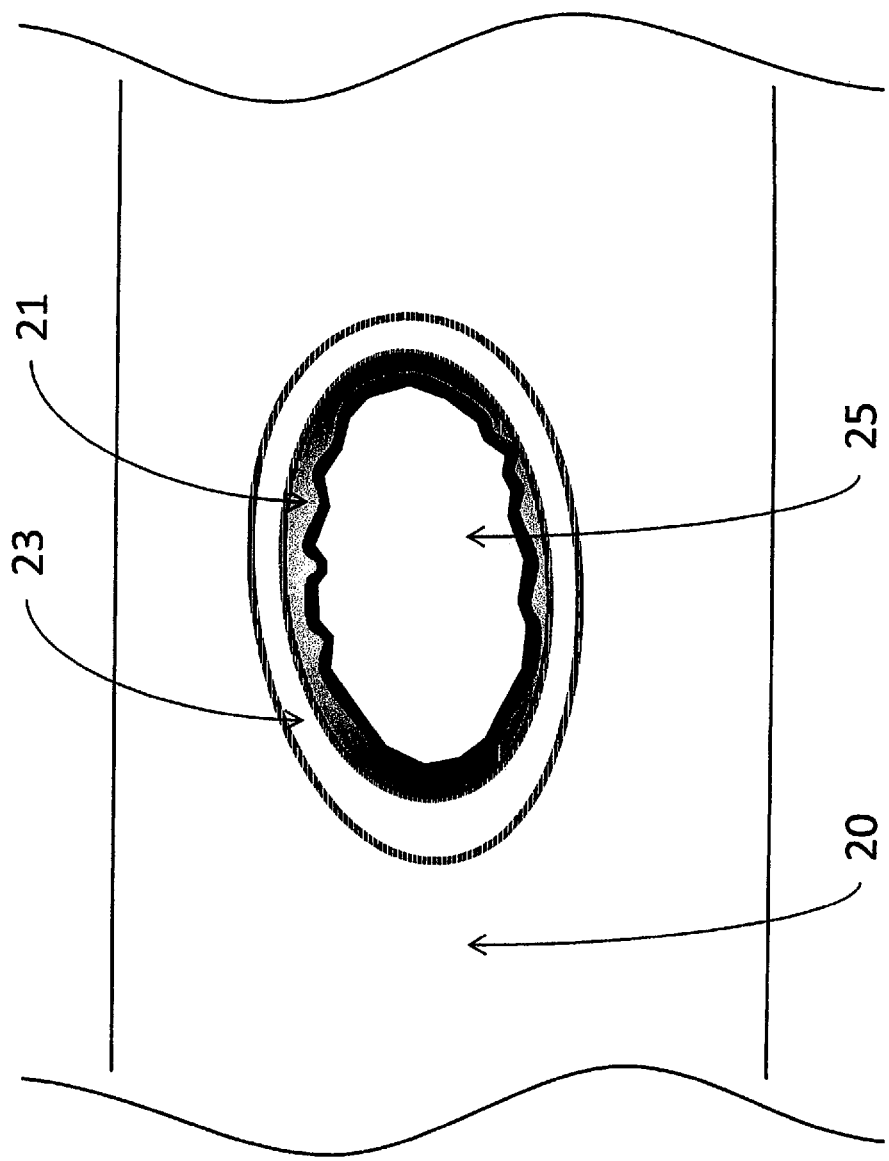
FIG. 10 is a diagram of an anastomosis creating using the devices and methods disclosed in the present application.

In one embodiment, the proximal base 10 is configured as shown in FIGS. 3a and 3b. The proximal base 10 is configured to receive the first heating element 8 (FIGS. 4a-4c), which is covered by the proximal heat spreader or heating surface 12. The heating surface 12 is comprised of a thermally conductive material which draws heat from the first heating element 8. Power attachment points 11 ensure that the heating element 8, in whichever illustrated configuration is selected, may be energized. The heating surface 12 transfers heat into the adjoining vessels to create a weld band 21 (FIGS. 9 and 10) and to cut tissue to create an anastomosis or fistula 25 (FIGS. 9 and 10). The size and shape of the weld zone and anastomosis can be altered by adjusting the shape of the heating surface 12. The geometry can also be altered such that the temperature is equal in the passive and active heated surfaces. In one preferred embodiment, the heating surface or proximal heat spreader 12 comprises an aluminum plate, although alternative thermally conductive materials such as aluminum nitride, ceramics, tungsten, steel, or beryllium may be used. The thickness of the heating surface 12 is approximately the thickness of the vessel in which the weld is being created. However, the thickness may be increased or decreased to control the amount of heat that is conducted into the surrounding tissue. Typical thickness of the heating surface ranges from 0.010 inches to 0.060 inches (FIGS. 3a-3b, 4a-4c).

In one embodiment as illustrated in FIG. 7b, a distal heat spreader 24 on the distal tip 5 has a plurality of raised segments 29 for forming a segmented rib 30. The segmented rib 30 creates a focused heat conduction path through the tissue, while gaps 31 between the segments 29 provide an insulative barrier that limits tissue dessication to promote adhesion without cutting. The size and number of segments 29 can be adjusted to control the rate of tissue dessication that may accommodate variable tissue thickness.

Figure 7C:
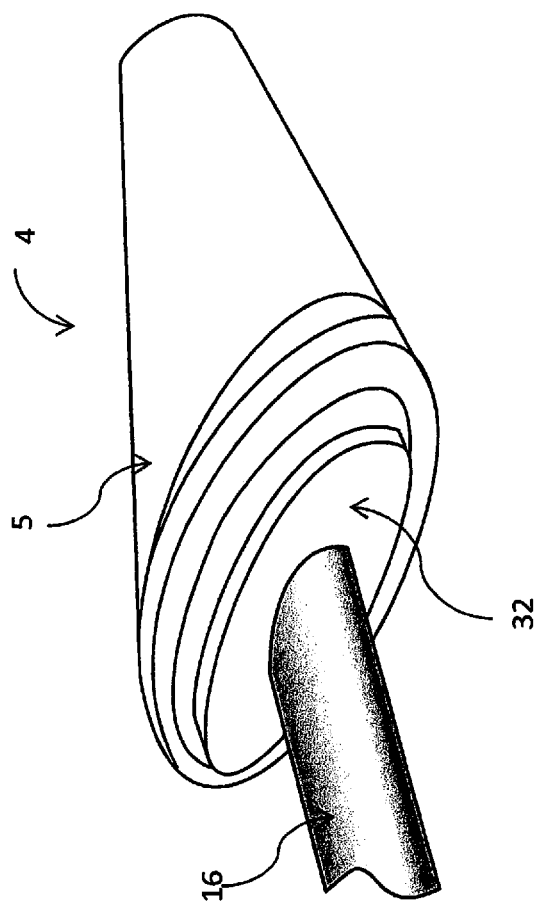
FIG. 7c is an isometric view similar to FIGS. 7a-7b of still another modified embodiment of the distal tip and heating assembly of the present invention.
Figure 8A:
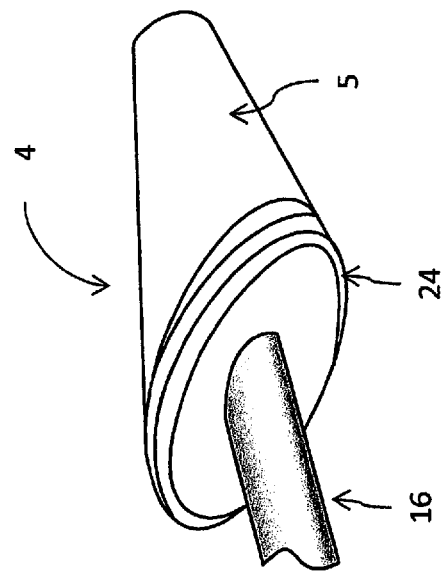
FIG. 8a is an isometric view similar to FIGS. 7a-7c of yet another modified embodiment of the distal tip and heating assembly of the present invention.
Figure 8B:
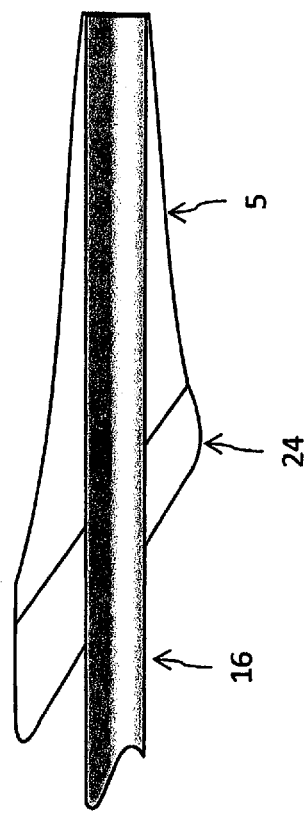
FIGS. 8b-8f are cross-sectional views of different embodiments of the distal tip and heating assembly of the present invention.
Figure 8E:
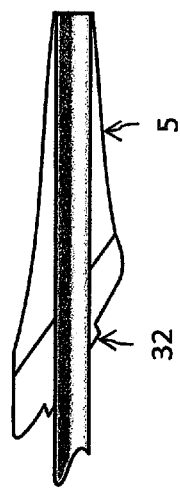
Figure 8D:
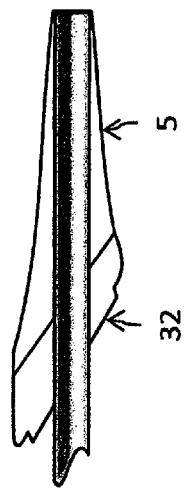
Figure 8C:
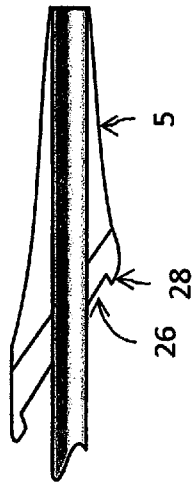

In another embodiment, as illustrated in FIGS. 7a and 8c, the passive heating element 24 has a raised outer rib 28 along its circumference. The raised outer rib 28 creates a pocket 26 in the center where tissue is captured and removed during the welding process. The outer circumference of the rib has a radius to create a transition between the weld band outside of the cut zone and the native tissue. A radius allows for minimal compression at the edge of the weld. This configuration provides a focused heat conduction path through the tissue between the active and passive heating assemblies to promote tissue cutting while the step gap provides an offset that limits tissue compression and dessication in the inner and outer regions to promote tissue adhesion without cutting in the adjacent zone.

Figure 8F:
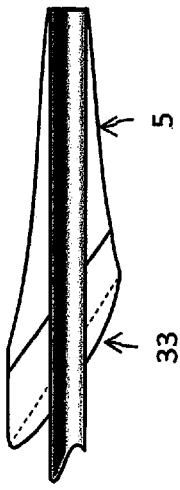

In still another embodiment as illustrated in FIG. 8f, the distal heating assembly 4 has a domed surface 33. The domed shape of the surface 33 creates a higher compression zone in the center to promote tissue cutting, while tapering off at the perimeter to promote tissue dessication and adhesion without cutting.

In another embodiment, as illustrated in FIGS. 7c and 8d, a raised surface 32 is designed to increase the compression force on the tissue in the center, while creating a wider weld band 21 (FIG. 9) around the perimeter. The wider weld band creates a stronger weld. The width of the raised center section may be adjusted to be narrower or wider in order to achieve the desired weld strength or anastomosis opening geometry. As illustrated in FIG. 8e, a slit between the two vessels can be created by making the raised surface 32 extremely narrow. As the surface area of the mating section of the distal heating assembly 4 is decreased, the amount of heat transferred from the active heater will decrease. This can be useful if less heat is needed between two different anatomical structures that are being welded. Another feature of a narrow raised section is a temperature gradient across the distal heating assembly 4 that increases radially from the raised section. A temperature gradient allows the heat to be the highest at the center, which completely denatures and cuts through tissue, creating an anastomosis. As the temperature decreases radially, the tissue has less necrosis, yet the proteins are denatured, which leads to a strong weld and long term healing.

The shape of the distal heating assembly 4, in combination with compression force, influences the rate at which the passive heating element cuts through the tissue. If too much heat or pressure is applied abruptly, distal heating assembly 4 may quickly cut through the tissue without transferring enough heat to the surrounding tissue to achieve a satisfactory weld. Instead, a balance of heat and pressure is required to dessicate and denature the protein in the tissue surrounding the cut to promote adhesion prior to cutting. In order to best achieve this balance, the temperature and position of the distal tip are monitored during the welding process and the heat and/or pressure being applied is adjusted to achieve the desired rate and to ensure that the distal heating assembly 4 and proximal heating assembly 2 are directly opposed to ensure complete weld fusion and aperture cutting. Different heat profiles may also be designated, based upon the starting tissue thickness prior to joining the tissue. In an embodiment as illustrated in FIG. 4b, heating element 8 is embedded in the conductive proximal heat spreader 12 that is a component of the proximal heating assembly 2 for tissue compression. Heating element 8 has a serpentine shape to increase the surface area in contact with the proximal heat spreader 12 to provide more effective heat transfer to the tissue to promote controlled dessication and adhesion without cutting through the tissue too rapidly.

In another embodiment, as illustrated in FIG. 4c, the active heating element within the proximal heating assembly 2 may be configured to have separate elliptical elements that provide independent power delivery for heating and cutting. The outer element can be configured to deliver reduced heat to promote controlled dessication and adhesion in the weld zone without cutting through the tissue, while the inner element can be configured to deliver increased heat to promote rapid cutting through the tissue in the cutting zone.

Figures 11A, 11B:
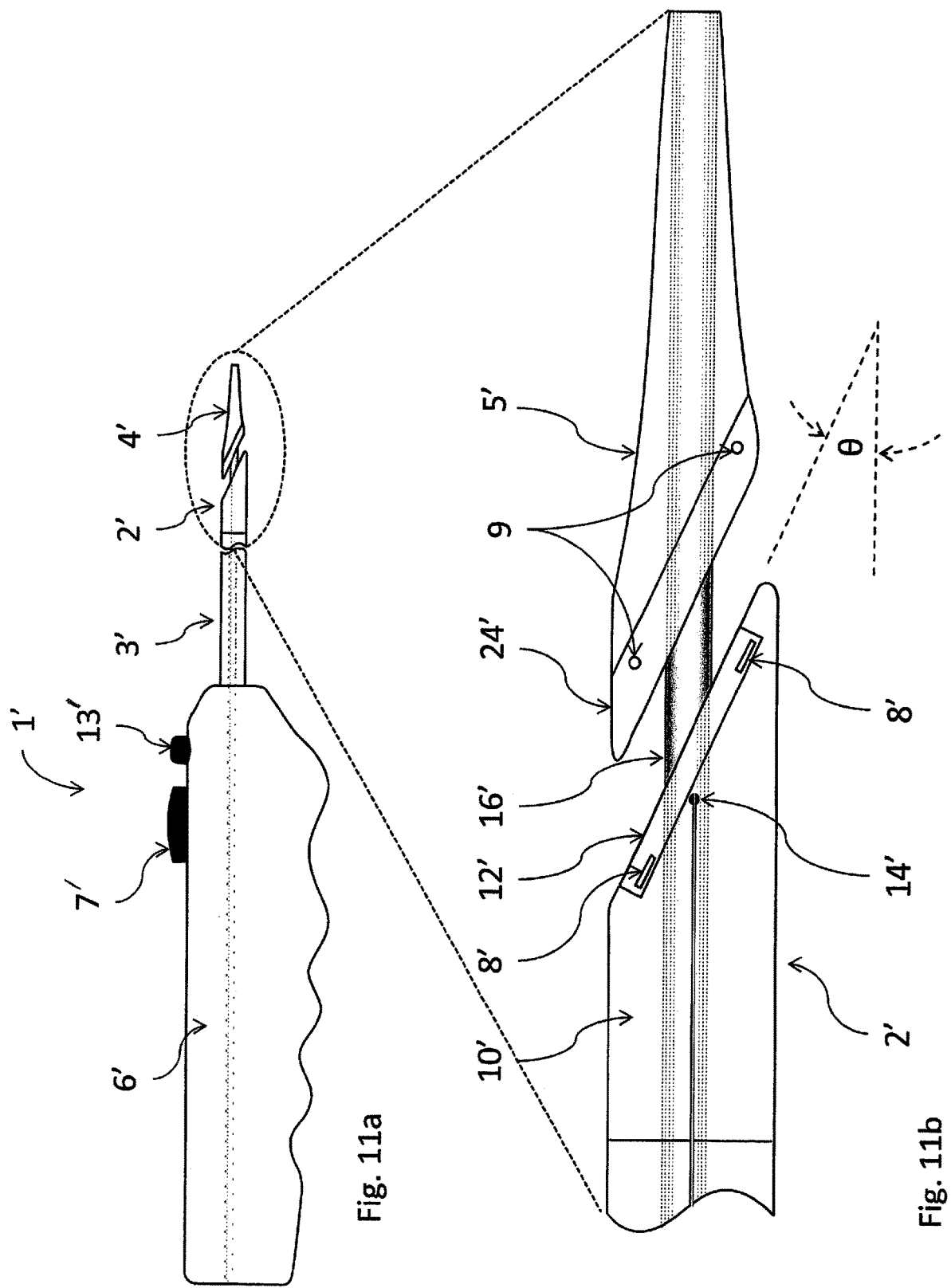

In a modified embodiment of the intraluminal anastomotic device 1', as illustrated in FIG. 11b, wherein like elements to those in the embodiment of FIGS. 1a and 1b are denoted by like reference numerals, primed, an active distal heating element 9 is embedded into the distal heat spreader 24', rather than the passive heat spreader 24 employed in the FIG. 1 embodiment. This is beneficial if separate heating profiles are required for different tissue types. For example, if joining a thick artery to a vein, it may be beneficial to apply more heat to the thick artery because it dissipates more heat and requires more energy to denature the tissue. Distal heating element 9 may be constructed similarly to the heating element 8' within the proximal heating assembly 2', and may have a closed loop temperature control so that temperature may be precisely controlled independently from heating element 8'. Alternatively, the distal heating element 9 can also be heated using electrodynamic inductive energy. In this case, a primary coil is integrated into the proximal heating assembly 2' and a secondary coil, which can be tuned to the same natural frequency, is embedded in the distal heating assembly 4'. As the proximal heating assembly 2' heats, current passes through the primary coil, creating a magnetic field which acts on the embedded coil in distal heating assembly 4', creating a current that heats the resistive element.

It is important for the proximal and distal heating assemblies 2, 2' and 4, 4' in both embodiments to have a non-stick surface to prevent denatured tissue from bonding to the device. If tissue bonds to the device, the weld between vessels can be damaged or weakened during removal of the device. Multiple different coatings or surface modifications can be applied to the components to create a non-stick surface. In one preferred embodiment, components of the device have a surface finish of <16 Ra and are coated using a high temperature Parylene. Other non-stick coatings, such as Poly Tetra Fluoro Ethylene (PTFE), Titanium Nitride (TiN), Chromium Nitride (CrN), Dicronite, silicone, or other similar coatings known to those skilled in the art may be used to prevent tissue adherence.

In the embodiments of FIGS. 3a and 3b, it is important that an inner tube 16 also have a non-stick surface to prevent coagulated blood and tissue from bonding to the surface and obstructing the annular gap between the outside diameter of the inner tube 16 and the inside diameter of the proximal heating assembly 2. If blood or tissue bonds to or obstructs this annular gap, this may prevent effective compressive force transmission to the distal heating assembly 4 and compromise tissue weld fusion or tissue cutting. In one preferred embodiment, the outside diameter of the inner tube 16 and inside diameter of the proximal heating assembly 2 1) have a surface finish of <16 Ra, 2) have an annular gap of 0.0005-0.0002 inches, and 3) are coated with a high temperature non-stick material as previously discussed.

The embodiment illustrated in FIGS. 2*a* and 2*b* provides distal tip feedback, wherein movement of the distal heating assembly 4 is converted to a signal by a position sensor 36 within the handpiece 6, or, alternatively, outside of the handpiece 6. This movement can then be displayed and/or utilized for a control algorithm. A signal that relays the absolute position of the distal heating assembly 4 from the position sensor 36 to a display device (not shown) of some type, through an output signal cable 34 is valuable for verifying the tip position throughout the procedure and for determining the thickness of the tissue between the tip and base of the catheter before, during, and after the formation of the fistula 25 (FIG. 10). The tissue thickness is related to the distance measurement by the equation $T=d \sin \theta$. The tissue thickness before the procedure can be correlated to the length of the fistula post-procedure. The relative position of the distal heating assembly 4 during the formation of the fistula 25 is also valuable and can be related to the rate of tissue dessication, cutting and welding. This signal may be used as an input to control heat application. For example, in FIG. 2*a*, the proximal heating assembly 2 and distal heating assembly 4 are spaced by a distance $d_1$, prior to the procedure. Based upon the type and thickness of the tissue through which the anastomosis is being created, and other factors related to functionality and durability of the fistula, tip position after the procedure can provide confirmation that the tissue was properly desiccated and both vessel walls have been cut. After the procedure, the tip is moved forward to a spaced position $d_2$ (FIG. 2*b*) for device extraction and the position of the tip can be verified using the sensor(s) 36.

Figure 5:
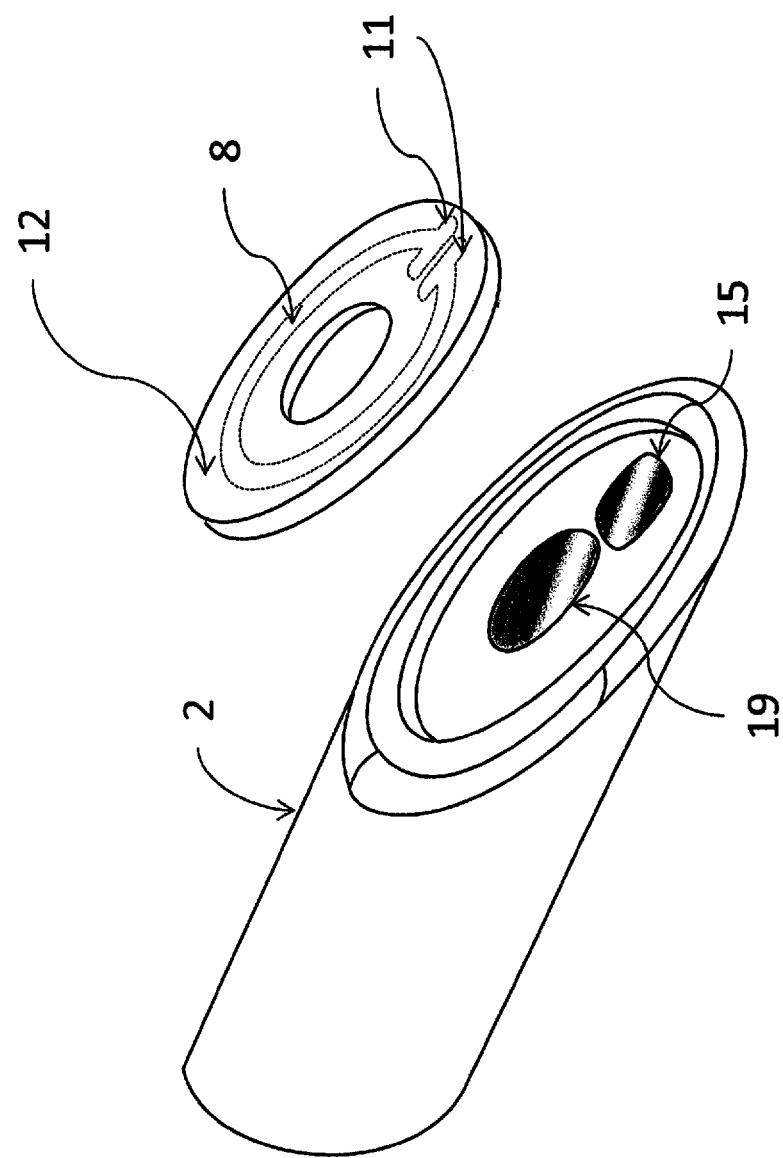
FIG. 5 is an exploded isometric view of another embodiment of the proximal base and heating assembly.

In FIG. 5, there is illustrated an embodiment of the proximal heating assembly 2 wherein the heating element 8 is comprised of tungsten, and that tungsten heating element is sandwiched between two ceramic layers, comprising together the proximal heat spreader 12.

Referring now particularly to FIGS. 9 and 10, a method for using the device 1, 1' will be discussed. To begin the inventive method of intravascular access and communication, the practitioner selects an appropriate procedural site having each of a primary blood vessel 20 and a secondary blood vessel 22 in close proximity to one another. In currently preferred approaches, the primary blood vessel 20 comprises a vein, and the secondary blood vessel 22 comprises an artery, but the invention is not limited to this arrangement. Initially, a piercing device is inserted into the primary vessel 20 and actuated to pierce the vessel walls and extend into the adjacent secondary vessel 22. Once penetration from primary blood vessel 20 to secondary blood vessel 22 has been achieved, the guidewire 17, preferably having a diameter of 0.014" or less, is advanced until the guidewire is positioned in the blood flow path of blood vessel 22 sufficiently to allow the piercing device to be removed while retaining the guidewire's position in blood vessel 22.

Once guidewire 17 is sufficiently in position as previously described, the practitioner withdraws the piercing device completely from the body, thus leaving the guidewire in the desired position and crossing from primary vessel 20 to secondary vessel 22. One exemplary piercing system and methods is disclosed in co-pending U.S. application Ser. No. 13/668,190, already expressly incorporated herein by reference, but any suitable piercing system and method may be used within the scope of the present invention.

Now, as disclosed, for example, in a manner similar to those disclosed in prior Provisional U.S. Application Ser. No. 61/596,670, already expressly incorporated herein by reference, the anastomosis using the embodiments of the present invention may be created. The guidewire 17 creates an access path for the device 1, 1'. The device 1, 1' is inserted into the patient by loading a proximal end of the guidewire 17 into the lumen 18 of tip 5. The device 1, 1' is advanced further into the patient, tracking over the guidewire 17, until the tapered dilating distal tip 5 comes into contact with the selected anastomosis site. The device 1, 1' can be tracked over the guidewire with the distal tip extended (as shown in FIG. 2*a*) or retracted (as shown in FIG. 2*b*). The distal heating assembly 4 is extended and further advanced into the second vessel 22 by advancing the inner tube 16 distally, thereby dilating the opening 25 in the vessel, so that the distal tip 5 is in the second vessel 22, and the proximal base 10 is in the first vessel 20, with its heat spreader surface 12 contacting the inner wall of the first vessel 20. At this juncture, the opening 25 formed in the adjoined walls of vessels 20 and 22 has recovered back to a smaller diameter and fits tightly around the device.

After the distal tip 5 is advanced into the second vessel 22, as illustrated in FIG. 9, a slight tension, or alternatively a slight pressure, is applied to the proximal heat spreader 12 to seat it against the vessel wall and promote vessel apposition. The blunt shape of the proximal end 24 of the distal tip 5 prevents the distal tip from inadvertently retracting back through the vessel wall. The proximal end 24 of the distal heating assembly 4 is then retracted to close the spacing between the respective proximal and distal heating assemblies, until the walls of the first and second vessels 20 and 22 respectively, are captured between the facing blunt surfaces of each of the proximal heat spreader 12 and the distal heat spreader 24.

A controlled tension is maintained between the distal tip 5 and the proximal base 10, and at this juncture, with the vessels securely clamped, energy is applied to the proximal heating element 8, as well as to the distal heating element 9 in the case of the modified embodiment 1'. As the heat elements weld and cut the vessels, the heat elements will move closer to one another. When fully retracted, the system is designed so that the two heat elements come into direct contact with one another to ensure a complete cut and capture of the vessel tissue to be removed. A variety of DC resistive energy profiles may be used to achieve the desired coaptation and cutting. For example, a rapidly stepped or ramped increase to achieve and maintain a desired temperature setting of 150° C.-350° C. may be applied to maximize welding prior to cutting. Energy may be modulated based upon the impedance of the tissue or temperature feedback. Different energy application durations, or cyclic pulses may be used to maximize welding and cutting, while minimizing heat transfer to adjacent tissues. The distal tip 5 is configured to have insulating properties to minimize heat transfer to adjacent tissues and/or fluids. The active heat element is a generally oval shape and cuts an anastomosis larger that the diameter of the proximal base 10. Within the oval shape of the cutting elements, there may be provided, if desired, a cavity for capturing the tissue that has been cut. As noted above, the entire surface of the proximal and distal heat elements is configured to have a non-stick coating, such as PTFE, to limit tissue adhesion.

Regarding the tissue welding process, more particularly, the DC resistive energy functions to fuse or weld the vessels together, creating an elongate aperture 25 (FIG. 10) through the opposing walls of each of the first and second vessels, as well as any intervening tissue. As formed, the elongate aperture may typically resemble a slit. However, as pressurized flow begins to occur through aperture 25, which creates a communicating aperture between the first and second blood vessels, the aperture widens in response to the pressure, taking the shape of an ellipse as it opens to form the desired fistula. The effect is illustrated in FIG. 10. The edges 21 of the aperture are cauterized and welded. Outwardly of the weld band 21 is a coaptation area 23. As shown, the cut area corresponds to the shape of the heating or cutting element. It can be of multiple shapes, such as round, oval, a slit, or a combination as shown. The area adjacent to the cut has been approximated and welded due to the flat face of the catheter in the vein (first vessel) being larger than the heating surface 12. The heat from the heating surface 12 is also preferably spread over this area by a conductive material that can be above, below or within the heating surface 12 or base 10. This creates a temperature gradient, which is a particularly advantageous feature of the present invention.

Once the fistula 25 has been fully formed, the entire instrument 1, 1' and guidewire 17 are withdrawn.

Other embodiments and approaches are contemplated, but not fully illustrated herein. For example, in certain applications, it may be advantageous to provide an outer lumen surrounding the proximal base 10 and tapered at the same angle. After the creation of the anastomosis 25, the outer lumen may be advanced until it comes into contact with the wall of the primary vessel 20. With slight forward pressure on the outer lumen, the proximal base and distal tip are retracted into the outer lumen. The outer lumen provides support to the surrounding tissue, and prevents the weld area from being damaged during the removal step. The outer lumen may be utilized in conjunction with any of the previously disclosed embodiments.

In an alternative method, after welding, the distal heating assembly 4 may be advanced to separate it and the proximal heating assembly 2. Prior to retracting the distal heating assembly 4 through the fistula 25, the distal heating assembly 4 is rotated 45-180 degrees such that the taper of the assembly is oriented to create a ramp when being retracted through the fistula.

In yet another alternative method, the tip can be retracted by keeping the distal and proximal heating assemblies 4 and 2, respectively, together, applying heat, and applying a retraction force to the device 1, 1'. The heat will cause the tissue to expand away from the catheter as it is removed.

Other optional alternative configurations are as follows:

1) External Inductive Activation Energy

An alternative embodiment may be constructed wherein inductive activation energy is supplied from outside, or external to, the body and does not have a direct electrical connection to the catheter. An emitter is placed in close proximity to the desired fistula location, adjacent to the catheter tip. The activation energy then travels through the skin and surrounding tissue without effect, but creates heat through reactive elements in the catheter tip and base.

2) Distal Tip Angle

Another alternative embodiment is contemplated wherein the catheter, with cylindrical shape, is comprised of a stationary base with movable tip, wherein the interface between the base and tip have a coplanar interface, and further wherein the angle ( ) of the interface is between 15 and 50 degrees.

3) Expandable Distal Tip

Another alternative embodiment may be provided wherein the distal tip is expandable to allow for a reduced area profile of the distal tip for entry into and exit from the adjacent vessel and an expanded area profile to increase the area of compression for vessel wall welding and cutting. It remains in the closed, or reduced area profile position as the catheter is advanced to the target site for the anastomosis and the distal tip enters the artery which limits potential trauma as the distal tip dilates through the vessel wall. Once the catheter is in place at the target site for the anastomosis, the distal tip is retracted toward the proximal tip and a compressive counter force from the proximal tip is applied to the rigid spreader faces of the distal tip, which cause them to pivot to the open position and apply a greater surface area of compression to the adjacent vessel walls captured between the proximal and distal tip.

Still another embodiment is contemplated wherein the distal tip is expandable to allow for a reduced area profile of the distal tip for entry into and exit from the adjacent vessel and an expanded area profile to increase the area of compression for vessel wall welding and cutting. The distal tip is comprised of a flexible elastomeric material such as silicone, though other materials may be used. In a manner similar to the previous embodiment, the catheter is positioned at the target site for the anastomosis in the reduced area profile position and the distal tip is retracted toward the proximal tip and a compressive counter force from the proximal tip is applied to the elastomeric material of the distal tip, which causes the distal tip to expand radially outward and apply a greater surface area of compression to the adjacent vessel walls captured between the proximal and distal tip.

4) Cooling Methods

An approach for cooling the proximal heating assembly 2 near the active heat element may be desired to prevent unintended heat transfer and necrosis to adjacent vascular tissue. To achieve this, it is desired to keep the surface temperature of the catheter components near the active and passive heat elements below 150 F. An embodiment is contemplated wherein an inner infusion lumen, which may be auxiliary lumen 15 shown in FIGS. 4 and 5, is employed in the catheter shaft that allows room temperature sterile saline to be infused through the inner lumen and exits the proximal tip near the active heat element. In this contemplated embodiment, the exit is within 2 mm of the active heat element, though the position can be up to 10 mm spaced from the active heat element. In one particular method, the saline flow rate is 3 cc/min, though the rate can be variable from 2-5 cc/min.

Another embodiment is contemplated wherein an outer infusion lumen is employed that allows room temperature sterile saline to be infused through the annular space between the catheter shaft and outer lumen and exit near the active heat element on the proximal tip. The lumen can be incorporated into the vascular access sheath, or can be incorporated separately. Like the previous embodiment, the exit is within 2 mm of the active heat element, though the position can be up to 10 mm away from the active heat element. In this method, the saline flow rate is 3 cc/min, though the rate can be variable from 2-5 cc/min.

Yet another embodiment utilizes a passive thermal conductive element, which is embedded in the proximal heating assembly 2 and provides a heat sink to shunt unintended heat from the active heat element and the plastic material of the proximal heating assembly 2, conducting it proximally in the catheter. The passive heat conductive element can be fabricated of aluminum, copper, stainless steel, ceramics and many other thermally conductive materials.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A device for creating an arteriovenous (AV) fistula, comprising:
   a proximal base having a distal tapered end surface;
   a distal tip connected to the proximal base and movable relative to the proximal base, said distal tip having a proximal tapered end surface;
   a first heating assembly comprising an energized heating element disposed on one of said distal tapered end surface or said proximal tapered end surface; and
   a second heating assembly comprising a passive non-energized heat spreader disposed on another one of said distal tapered end surface or said proximal tapered end surface;
   wherein the distal tapered end surface and the proximal tapered end surface are adapted to contact opposing sides of a tissue portion to create the AV fistula; and
   wherein the passive non-energized heat spreader comprises a plurality of raised segments forming a segmented rib for creating a focused heat conduction path through the tissue portion.

2. The device as recited in claim 1, wherein said distal tapered end surface is oriented at an angle of 15-90 degrees relative to a longitudinal axis of said device.

3. The device as recited in claim 2, wherein said distal tapered end surface is oriented at an angle of 15-50 degrees relative to said longitudinal axis.

4. The device as recited in claim 3, wherein said distal tapered end surface is oriented at an angle of approximately 23 degrees relative to said longitudinal axis.

5. The device as recited in claim 1, wherein a taper of said proximal tapered end surface matches a taper of said distal tapered end surface, so that the distal and proximal tapered end surfaces match one another and fully engage with one another when engaged.

6. The device as recited in claim 1, and further comprising a shaft for connecting the distal tip to the proximal base, the shaft being extendable and retractable to extend and retract said distal tip relative to the proximal base.

7. The device as recited in claim 6, wherein each of the first and second heating assemblies comprise non-stick surfaces.

8. The device as recited in claim 7, wherein the shaft also comprises a non-stick surface.

9. The device as recited in claim 8, wherein the non-stick surfaces of the first and second heating assemblies and the shaft have a surface finish of less than 16 Ra.

10. The device as recited in claim 1, wherein the one of said distal tapered end surface or said proximal tapered end surface on which the first heating assembly is disposed has a second passive non-energized heat spreader disposed thereon.

11. The device as recited in claim 10, wherein the passive non-energized heat spreader comprises a thermally conductive material which extends across a substantial portion of the one of said distal tapered end surface or said proximal tapered end surface on which it is disposed, the passive non-energized heat spreader being in thermal contact with the energized heating element to draw heat from the energized heating element and spread the heat across the respective distal or proximal tapered end surface.

12. The device as recited in claim 11, wherein the passive non-energized heat spreader is constructed so that it has a thickness approximately equal to a thickness of a vessel in which the device is deployed, said thickness falling within a range of 0.010 inches to 0.060 inches.

13. The device as recited in claim 1, wherein the energized heating element comprises a serpentine configuration.

14. The device as recited in claim 1, and further comprising a temperature sensor near the energized heating element for providing closed loop temperature control to the first heating assembly.

15. The device as recited in claim 1, wherein the distal tip comprises a tapered outer surface, tapering down from the proximal tapered end surface toward a distal end thereof, the distal end of the distal tip comprising an aperture for a through lumen for receiving a guidewire, wherein a width of the distal tip at the lumen aperture is approximately equal to a diameter of the guidewire.

16. The device as recited in claim 1, wherein the energized heating element comprises separate elliptical elements that provide independent power delivery for heating and cutting.

17. The device as recited in claim 16, wherein the separate elliptical elements comprise an outer element and an inner element, the outer element being configured to deliver reduced heat to promote controlled desiccation and adhesion in a weld zone without cutting through tissue and the inner element being configured to deliver increased heat to promote rapid cutting through tissue in a cutting zone.

18. The device as recited in claim 1, wherein the first heating assembly is disposed on the distal tapered end surface and the second heating assembly is disposed on the proximal tapered end surface.

19. The device as recited in claim 18, and further comprising a second active energized heating element on the proximal tapered end surface.

20. The device as recited in claim 19, wherein the second active energized heating element is embedded into the passive non-energized heat spreader.

21. The device as recited in claim 1, and further comprising a position sensor for monitoring movement of the distal tip.

22. The device as recited in claim 1, wherein the segmented rib further comprises gaps between the plurality of raised segments, said gaps providing an insulative barrier that limits tissue desiccation to promote adhesion without cutting.

* * * * *